United States Patent [19]
Forsberg

[11] Patent Number: 5,975,373
[45] Date of Patent: Nov. 2, 1999

[54] LIQUID SAMPLE COLLECTION AND TRANSPORT SYSTEM

[75] Inventor: Bengt Erik Forsberg, Etobicoke, Canada

[73] Assignee: Starplex Scientific, Ontario, Canada

[21] Appl. No.: 08/897,301

[22] Filed: Jul. 21, 1997

[51] Int. Cl.⁶ .................................................. B65D 37/00
[52] U.S. Cl. ..................... 222/209; 222/212; 222/312.6; 222/541.5; 141/351
[58] Field of Search .................................... 222/222, 209, 222/320, 321.6, 541.5; 141/351, 352, 311 A; 604/407

[56] References Cited

U.S. PATENT DOCUMENTS

| | | | |
|---|---|---|---|
| 329,920 | 11/1885 | Luedemann | 222/541.5 |
| 1,152,601 | 9/1915 | Carpenter | 222/209 X |
| 2,143,661 | 1/1939 | Schrader | 222/209 X |
| 2,742,202 | 4/1956 | Dresden et al. | 222/541.5 |
| 3,066,833 | 12/1962 | Hershenson | 222/209 X |
| 4,442,958 | 4/1984 | Amos | 222/320 X |
| 4,776,496 | 10/1988 | Battegazzore | 222/209 |
| 4,917,867 | 4/1990 | Jensen et al. | |
| 5,163,583 | 11/1992 | Whitworth | 222/209 X |
| 5,312,009 | 5/1994 | Ratajczak et al. | |
| 5,395,590 | 3/1995 | Swaniger et al. | |
| 5,460,283 | 10/1995 | MaCartney et al. | |
| 5,678,736 | 10/1997 | Hansen | 222/209 |
| 5,697,522 | 12/1997 | Mayes | 222/209 X |

*Primary Examiner*—Kenneth Bomberg
*Attorney, Agent, or Firm*—Merchant & Gould P.C.

[57] ABSTRACT

A lid for a liquid sample container is provided which includes an opening for transferring the sample into a further container for conducting the necessary tests and a flexible portion, which allows the sample to be expelled through the opening. The opening is normally closed by a detachable closure which can also be used to re-seal the opening after the desired quantity of the sample has been withdrawn. An apparatus is also provided for obtaining dual liquid samples, which comprises two sample containers, wherein one container is retained within a recess in the other to result in a unitary structure. Further a method of obtaining liquid samples is provided which utilizes containers of the present invention.

6 Claims, 5 Drawing Sheets

LIQUID SAMPLE COLLECTION AND TRANSPORT SYSTEM

Background of the Invention

1. Field of the Invention

The present invention relates generally to devices for collecting and transporting liquid samples. More particularly, the subject devices are used for collecting and transporting samples of liquids for analytical testing.

2. Description of the Prior Art

The sampling of fluids for diagnostic or evidentiary purposes is very common. Such fluids, which include urine, blood, water, milk etc., are collected in a specimen container and transported to a laboratory where they are analyzed to determine the presence of infections or contaminants such as drugs, alcohol etc. Under such circumstances, the collected sample must be maintained uncontaminated until the various testing procedures have been concluded. Containers for this purpose are common and usually comprise a plastic container having a secure lid.

The first step in analyzing the sample is normally the extraction of an aliquot of the collected fluid. Since the collected samples may pose a biohazard risk, great care must be taken to ensure that the liquid sample is not spilled during the handling of the container or the extraction of the desired aliquot. Further, in order to protect the accuracy of the analytical results, it must be ensured that no contaminants mix with the sample.

It is now preferred for the analytical process to be automated which involves the use of robotics to handle the specimen container and to conduct the various chemical and biochemical tests on the liquid sample. To conduct the desired tests, an aliquot of the sample is extracted from the vial and passed into a testing chamber (a test tube for example). As mentioned above, it must be ensured that the fluid sample is not spilled onto any part of the apparatus and that, during the extraction of such aliquot, another sample or other material does not contaminate the sample. Thus, specimen containers must be designed to be suitable for use in both manual and automated analytical processes.

Another issue arises in cases where biological samples are collected for evidentiary purposes. In such situations, the established protocols call for two samples of fluid to be collected and maintained in separate containers. One of such samples proceeds through the analytical process while the second is maintained uncontaminated for later reference if needed. In these cases it is important to maintain a proper chain of custody of the two samples so as to prevent tampering. Normally, the sample is collected in a collection cup and separated into transport containers, which are attached together, usually by rubber bands, until they reach the laboratory. Although the containers are labeled, they can easily be misplaced rendering further verification of the tests impossible and corrupting the chain of custody.

To address the safe transfer of the desired aliquot of the sample, various modifications to the container lid have been proposed. An example of such modification is described in U.S. Pat. No. 5,395,590 wherein Swaniger et al. teach a valved plastic lid for a specimen container. The '590 lid includes a valved opening in the center which comprises a number of slits, which, due to the elasticity of the plastic material, are normally closed. However, upon applying an inward force to the lid, the slits open and allow the contained fluid to pass through. In extracting fluid from a container having such lid, the opening of a second container, such as a test tube, is placed over the opening in the lid and the two containers are inverted. The first container is then forced downward thereby causing the slits in the lid to open and allowing fluid to enter the second container. However, the lid taught in the '590 patent has certain disadvantages. For example, the slits in the lid can be forced open prior to the testing process by applying pressure thereto and thereby allowing contaminants to enter the container. Similarly, the collected sample may also be inadvertently spilled thereby requiring a separate closure until the sample is extracted. Further, the manufacture of such a complicated structure adds to the cost of such a lid.

In U.S. Pat. No. 4,917,867, Jensen et al. teach an apparatus for the collection of dual biological samples. This reference describes a kit comprising a container containing two sample vials and other items to obtain the desired samples. After collecting the samples, the vials are placed back into the main container. Although accounting for the chain of custody during transfer, the apparatus of this reference requires the separation of the sample vials prior to the analysis process thereby resulting in the possibility of one of them being misplaced.

Thus a need exists for a specimen container which overcomes the above-identified deficiencies in the known devices.

SUMMARY OF THE INVENTION

Therefore the present invention provides, in one aspect, a flexible lid for a container containing a liquid, the lid comprising:

a means for securing the lid to the container to form a seal therebetween;

a spout having an opening for transferring the liquid to a second container;

a removable closure for the opening, the closure maintaining the opening in a normally closed state; and, a flexible portion surrounding the spout which permits the spout to move inwardly into the container whereby the liquid is expelled through the opening after removal of the closure.

In another aspect, the invention provides an apparatus containing liquid samples comprising:

a first container having a receptacle and a lid;

the first container receptacle having an internal cavity opening to the bottom of the first container;

a second container having a receptacle and a lid;

the second container being received within the cavity in the first container receptacle and being releasably secured within the cavity.

In yet another aspect, the invention provides a method of collecting and testing liquid samples using a collection container including a flexible lid, the lid comprising:

a means for securing the lid to the collection container to form a seal therebetween;

a spout having an opening for transferring the liquid to a testing container;

a removable closure for the opening, the closure maintaining the opening in a normally closed state; and, a flexible portion surrounding the spout which permits the spout to move inwardly into the collection container whereby the liquid is expelled through the opening after removal of the closure the method comprising:

a) removing the lid, transferring the sample into the collection container and securing the lid on the collection container;

b) transporting the collection container to a testing area;

c) removing the closure on the lid thereby exposing the opening;

d) locating a testing container above the opening and bringing the testing container into contact with the lid whereby the opening opens into the testing container;

e) inverting the testing and collection containers;

f) moving the testing and collection containers towards each other whereby the lid is flexed inwardly towards the interior of the collection container thereby expelling a controlled portion of the sample into the testing container;

g) separating the collection container from the testing container; and, h) proceeding with the required tests on the portion of the sample in the testing container.

BRIEF DESCRIPTION OF THE DRAWINGS

These and other features of the preferred embodiments of the invention will become more apparent in the following detailed description in which reference is made to the appended drawings wherein.

DESCRIPTION OF THE PREFERRED EMBODIMENTS

Figure 1:
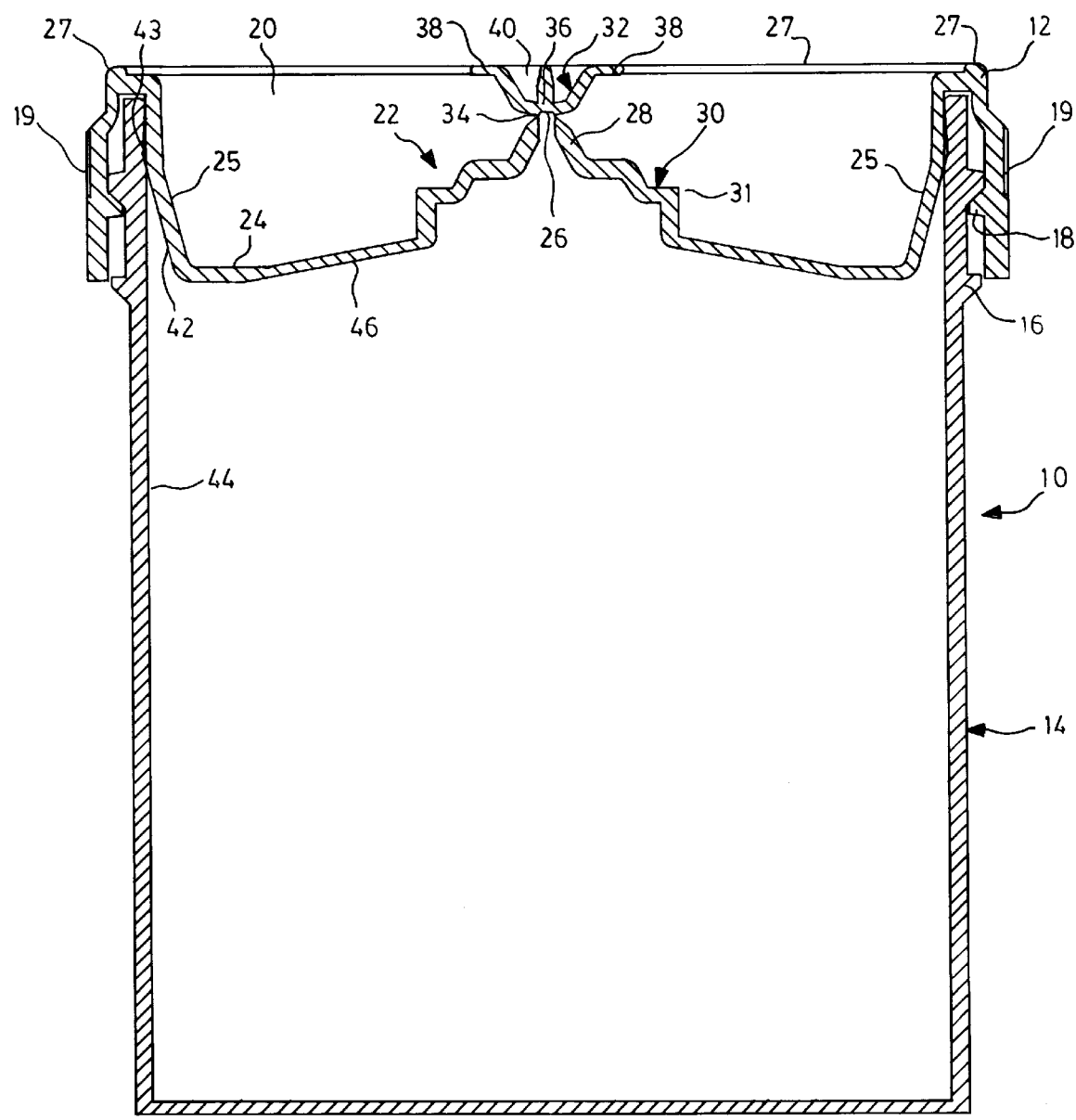
FIG. 1 is a cross sectional view through the central longitudinal axis of a specimen container in accordance with one embodiment of the present invention.

Referring to FIG. 1, a specimen container in accordance with a first embodiment is shown generally at 10. The container includes a lid 12, according to an embodiment of the invention, and a receptacle 14 for containing the liquid sample. The receptacle 14 is of a standard design and includes a threaded upper portion 16 which engages a corresponding threaded portion 18 of the lid 12, thereby allowing the lid to be secured to the receptacle. In the preferred situation, the lid is formed of a flexible thermoplastic material and the receptacle is of a generally cylindrical structure also formed of a thermoplastic material. Preferably, both the lid and receptacle are formed of polypropylene to allow for recycling of the materials.

In the embodiment shown in FIG. 1, the lid 12 includes a well 20 and a spout portion 22 located in the center of the lid. The well 20 of the lid 12 is bounded by a bottom surface 24 and a sidewall 25. Bottom surface 24 generally slopes upward from its junction with the sidewall 25, at the outer circumference, to the center spout portion 22. The spout portion 22 comprises a funnel 28 having an opening 26. The spout portion further comprises an uneven bearing surface 30 the purpose of which is described below. Bearing surface 30, in a preferred embodiment, has a plurality of ribs 31 that radiate in a direction towards the outer circumference of the lid. In an alternative embodiment, the ribs may be replaced by grooves.

The opening 26 is dimensioned so that, when the container 10 is inverted with the closure 32 removed, air cannot enter the container due to the surface tension of the liquid contained within. Accordingly, the liquid is prevented from exiting the container. For example, for samples comprising water or aqueous solutions, the opening 26 has a diameter of $\leq 0.04$ in. For other liquids, the diameter of the opening 26 will depend upon its surface tension.

The opening 26 is sealed by a closure 32, which is integrally formed with the lid 12 and is connected to the funnel 28 by means of ajunction 34. The junction 34 is made of the same thermoplastic material as the funnel 28 and the closure 32 but is of a thinner construction. The weakness of the junction 34 allows the closure 32 to be separated from the funnel 28 upon application of sufficient force. The closure 32 includes a pin 36 and a plurality of projections 38, which facilitate the manual, or automated gripping of the closure 32. In a preferred embodiment, the projections 38 comprise a plurality of arms that extend upwardly and radially thereby forming a concave region 40 around the pin 36. Alternatively, the projections 38 can consist of ribs.

The outer surface 42 of the side wall 25 includes a rim 43 which extends radially outward of the lid 12 and which bears against the inner surface 44 of the receptacle 14 to form, preferably, an air tight seal therewith when the lid is engaged on the receptacle. The bottom surface 24 of the well 20 includes a weakened portion 46 between the sidewall 25 and the spout portion 22. The weakened portion is formed by reducing the thickness of the thermoplastic material in the desired region. Thus, the bottom surface of the lid is made flexible in the region of the weakened portion 46 for the purpose described below.

Preferably, the outer surface 19 of the lid 12 includes conventional vertical ribs to aid in detaching the lid from the receptacle 14.

Further, in the preferred embodiment, the closure 32 does not extend above the rim 27 of the lid 12 so as to permit stacking of the containers 10 and the application of a security sealing tape, when necessary.

In operation, the lid 12 is removed from the receptacle 14, a fluid sample is introduced and the lid is secured to the receptacle. For withdrawing the desired aliquot of the sample, the closure 32 is twisted causing the junction 34 to break and thereby exposing the opening 26. The projections 38 assist in removal of the closure 32 by providing leverage for such twisting motion. A test tube (not shown) or other similar container for receiving the aliquot is inverted and placed over the spout portion 22 so that the rim of the opening of such test tube rests on the uneven bearing surface 30. Both the specimen container 10 and the test tube are then inverted thereby causing the fluid sample to fill the spout portion 22 and particularly the funnel 28. Since air is prevented from entering the container 10, the fluid sample does not leak from the opening 26. To extract the aliquot, the specimen container 10 and/or the test tube are moved towards each other causing the weakened portion 46 to flex inwardly and, in turn, forcing the spout portion 22 towards the interior of the receptacle 14. The inward movement of the spout portion 22 leads to an increase in pressure within the receptacle which, in turn, forces a portion of the fluid in the container to exit the opening and to collect in the test tube. The weakened portion 46 can be designed to deliver a specific, or controlled, volume of liquid. This is achieved by designing the weakened portion to flex by a specified amount.

The ribs 31, on the uneven bearing surface 30 of the lid, provide channels for the air in the test tube to escape when displaced by the entering fluid.

The specimen container is then separated from the test tube and turned upright. This removes the inward force on weakened portion 46 causing it to resume its normal raised position thereby reducing the internal pressure of specimen container 10. The vacuum created within the container due to such pressure drop causes any liquid remaining in the opening 26 and any drop clinging to the opening to be sucked back into the receptacle and prevents any further fluid from dripping out of the opening 26.

In order to prevent spillage of the sample fluid after the above process, the opening 26 is closed by heat sealing. In the preferred method, the heat sealing step involves the application of a foil over the opening and the application of heat onto the foil. In such manner, the heating source does not come into contact with the opening and prevents such source from being contaminated by the sample. In the alternative, the closure 32 may be inverted and the pin 36 inserted into the opening 26. To accommodate the latter closing method, the region 40 is designed to cover the funnel 28.

As mentioned previously, these testing steps can be carried out in an automated process wherein robotics are used to manipulate the containers, test tubes and other components.

In another embodiment, the test tube need not be in contact with the lid 12. In this embodiment, the contained fluid can be expelled in the same manner as above but by using a retaining device to support the container 10 above the test tube.

Figure 2:
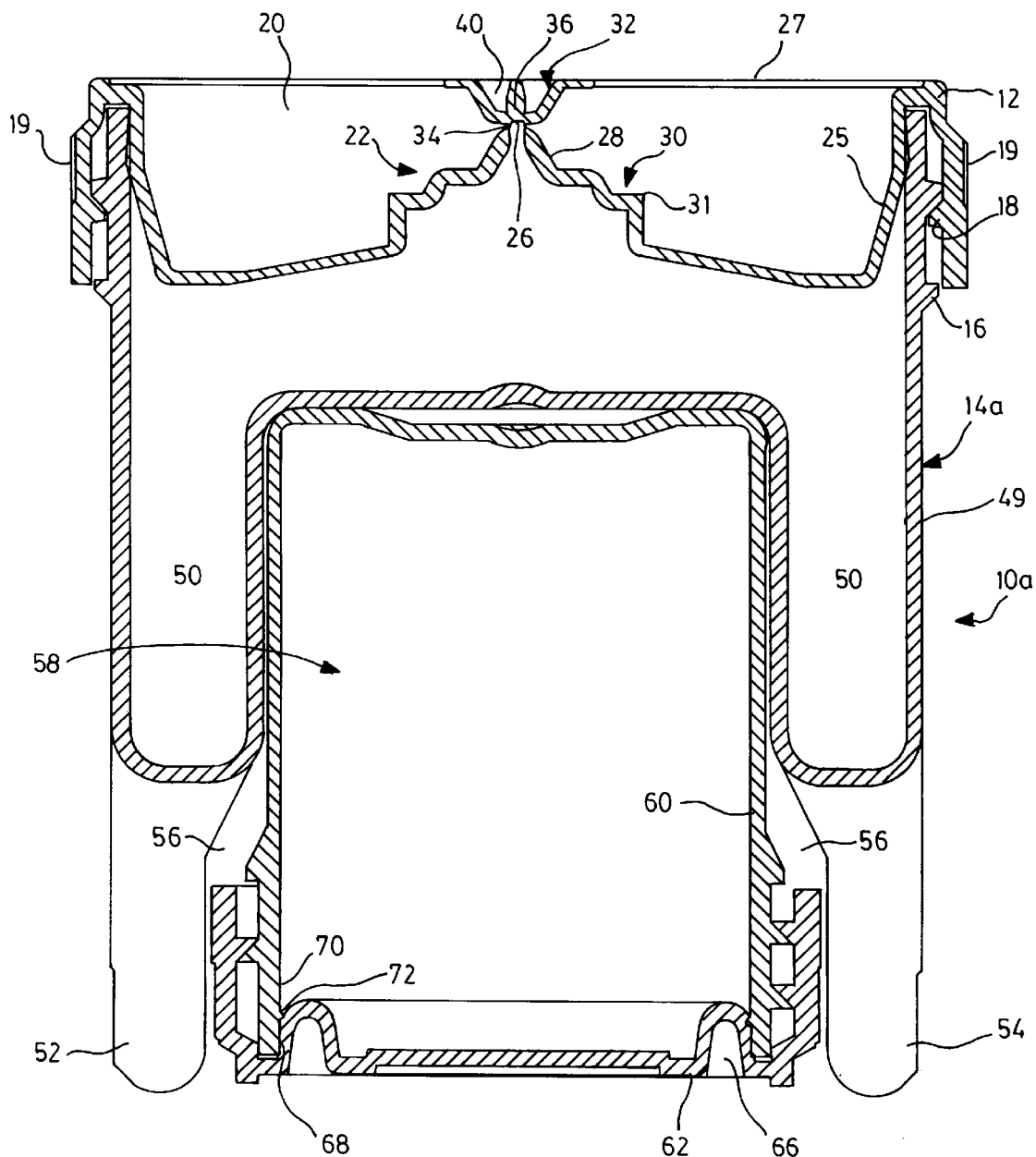
FIG. 2 is a cross sectional view of a specimen container in accordance with another embodiment of the present invention.

FIG. 2 illustrates a further embodiment of the present invention for handling a fluid sample, which has been transferred into two separate containers. In this embodiment, like elements are indicated with like reference numerals and the letter "a" is added for clarity. The specimen container according to this embodiment is indicated generally at 10a. The complete specimen container includes a first fluid sample container 49 having a lid 12 such as described above. Alternatively, the lid for the first container 49 can be any conventional lid known in the prior art. In the embodiment shown, the generally cylindrical first container 49 also includes a fluid sample receptacle 14a comprising a fluid containing chamber 50 and legs 52 and 54 which define a generally cylindrical recess 56. A second fluid sample container 58 is disposed within the recess 56. The second container 58 comprises a receptacle 60 and a lid 62. As above, the lid 62 is screwed onto the receptacle 60. To ensure that separation of the two containers does not occur, the exterior surface 64 of the second container 58 and the surface of the recess 56 are ribbed so as to provide a friction fit there between.

The lid 62 of the second container 58 includes an annular recess 66 around its outer edge and directed towards the interior of the receptacle 60. A lid of this structure is described in U.S. Pat. No. 5,460,283. The recess 66 is positioned so that, when the lid 62 is engaged on the receptacle 60, the outer wall 68 of the annular recess 66 is pressed against the inner wall 70 thereby forming a seal between the lid 62 and the receptacle 60 to prevent leakage of the contained liquid. In an alternative embodiment, a conventional lid may be used for the second container 58. In another embodiment, a rim 72 may be provided on the inner wall 70 of the receptacle 60. The rim 72 is then biased against the outer wall 68 of the recess 66 when the lid is secured.

In the preferred embodiment, the second container 58 does not extend beyond the legs 52 and 54 of the first container so as to enable the complete specimen container 10a to stand on legs 52 and 54.

Figure 3:
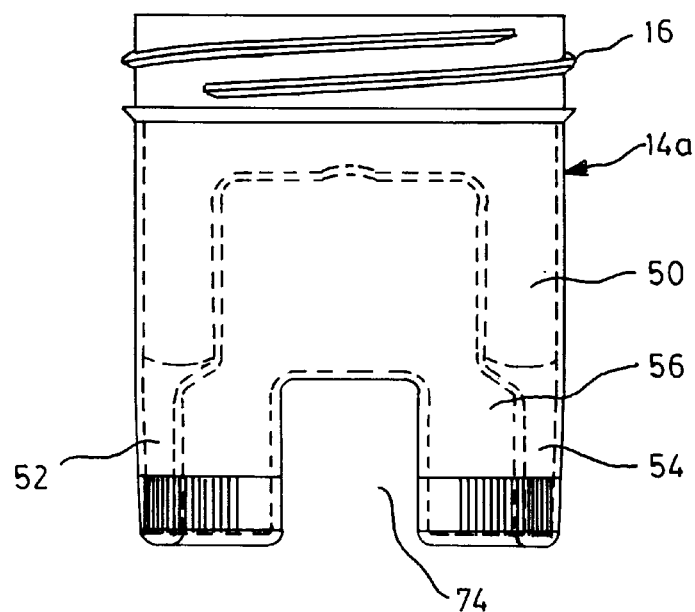
FIG. 3 is a side view of the container of FIG. 2 with the lid removed.
Figure 4:
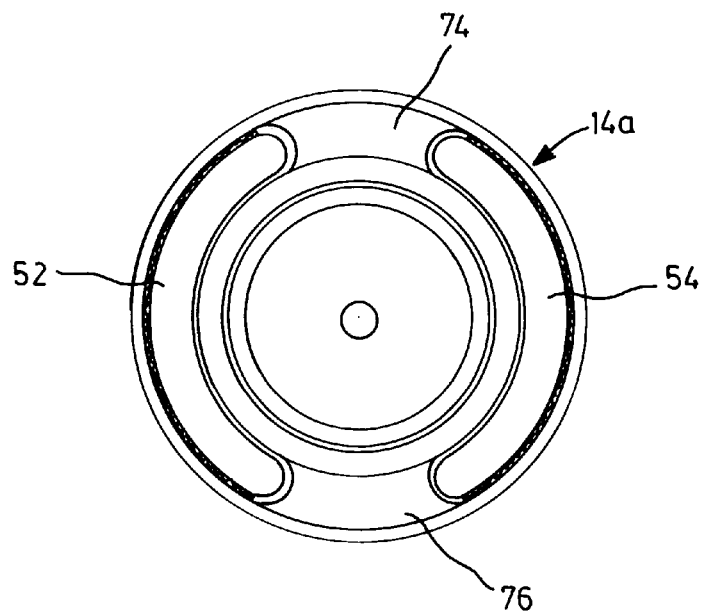
FIG. 4 is a bottom view of the container of FIG. 3.

FIGS. 3 and 4 illustrate different views of the receptacle 14a. As shown the legs 52 and 54, when viewed on end, are generally crescent shaped and follow the outer generally cylindrical surface of the receptacle 14a. The receptacle 14a includes two slots 74 and 76 located between legs 52 and 54. Slots 74 and 76 allow the lid 62 of the second container 58 to be grasped so as to permit extraction of the second fluid container 58 from the recess 56 of the first fluid container 49.

In a further embodiment, the second fluid container 58 may be screwed into the recess 56 instead of using the friction fit as mentioned above.

In using the dual container 10a as described above, the second container 58 is first separated from the first container 49 and both lids 12 and 62 are removed. The liquid sample is transferred into receptacles 50 and 60. Both lids 12 and 62 are replaced onto to the respective receptacles 50 and 60 and the second container 58 is inserted into the recess 56 as shown in FIG. 2. The first container 49 contains the sample to be tested while the second container 58 contains a duplicate sample for future reference. During the testing process, the steps discussed above are followed.

Figure 5:
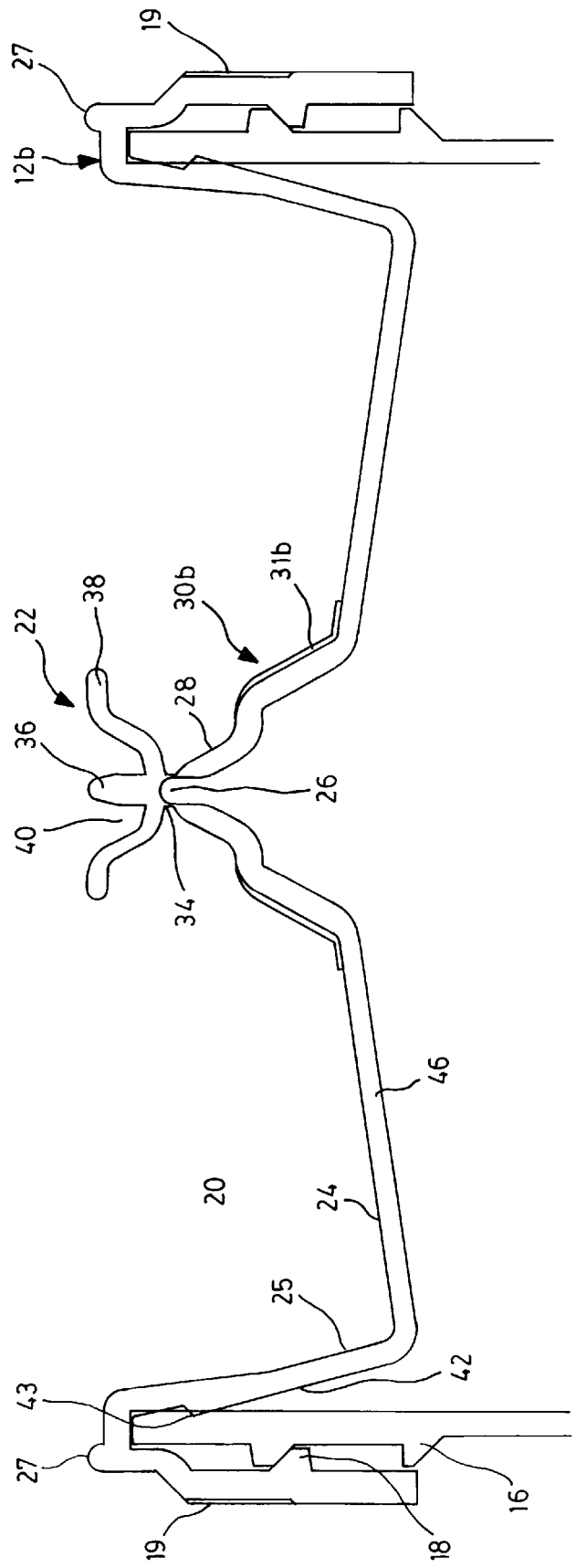
FIG. 5 is a cross sectional view of a sample container lid in accordance with another embodiment.

A further, preferred embodiment of the lid is shown in FIG. 5 wherein like elements are identified by like reference numerals and wherein the letter "b" is used for clarity. The lid of this embodiment is shown at 12b. The lid 12b has most of the same components as the previous embodiment of the lid 12 described above. However, the bearing surface 30b of this embodiment generally follows the slope of the funnel 28. The bearing surface 30b includes ribs 31b to provide an uneven surface as described above.

Figure 6:
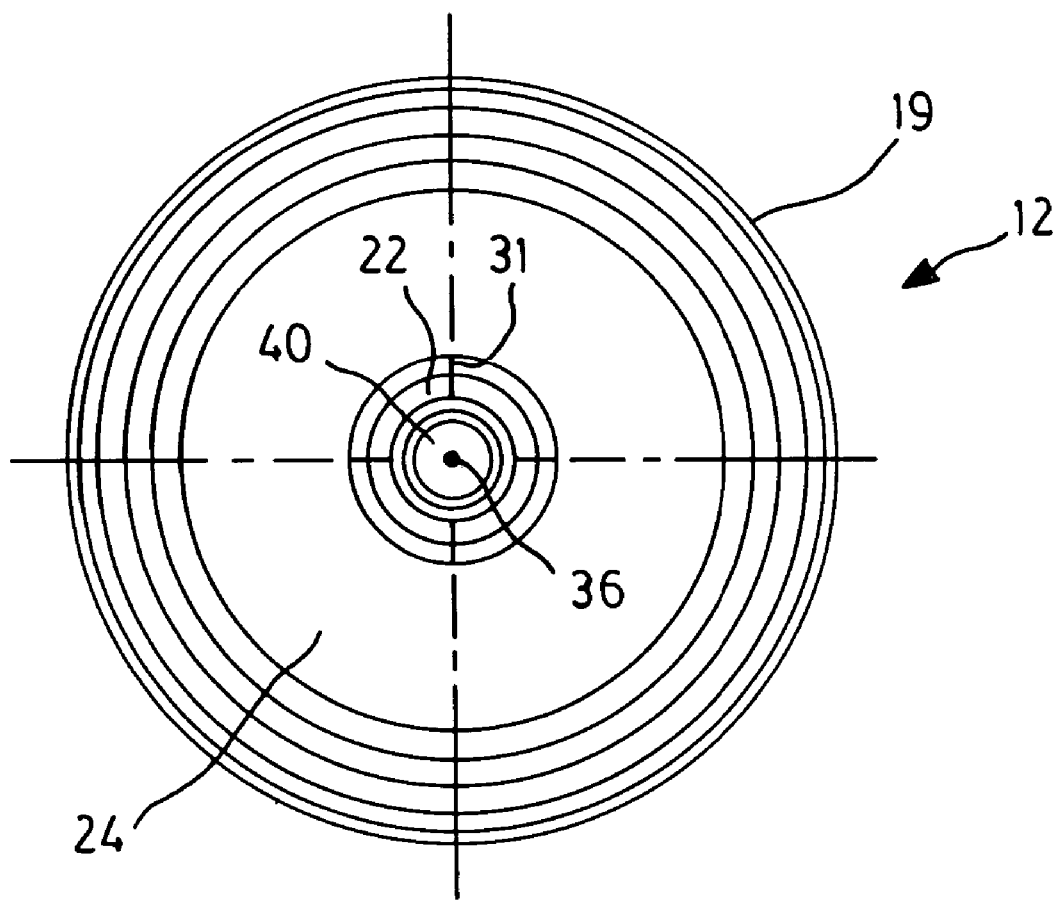
FIG. 6 is a top view of the lid for the container of FIGS. 1 or 2.

FIG. 6 is a top view of the lid 12 and illustrates the ribs 31 of the bearing surface 30. As shown, four ribs are provided which radiate outwardly from the center of the lid.

In another embodiment, the lids 12 and 12a can also be secured to the receptacle 14 by a snap fit.

Although the invention has been described with reference to certain specific embodiments, various modifications thereof will be apparent to those skilled in the art without departing from the spirit and scope of the invention as outlined in the claims appended hereto.

The embodiment of the invention in which an exclusive property Or privilege is claimed are defined as follows:

1. A flexible lid for a container containing a liquid, said lid comprising:

a means for securing said lid to said container to form a seal therebetween;

a spout having an opening for transferring said liquid to a second container;

a removable closure for maintaining said opening in a normally closed state, wherein said closure is integrally formed with said lid and is separable therefrom, a flexible portion surrounding said spout which permits said spout to move inwardly into said container whereby said liquid is expelled through said opening after removal of said closure; wherein said flexible portion includes a bearing surface surrounding said spout for bearing against an opening in said second container during the liquid transfer process.

2. A lid as claimed in claim 1 wherein a weakened portion joins said closure to said lid, said weakened portion being breakable thereby permitting separation of said closure from said lid.

3. A lid as claimed in claim 2 wherein said closure, after being removed, can be replaced on said opening for sealing said opening.

4. A lid as claimed in claim 3 wherein said closure includes projections for providing leverage when separating said closure from said lid.

5. A lid as claimed in claim 1 wherein a top portion of said lid is recessed into the interior of said container.

6. A lid as claimed in claim 1 wherein said bearing surface includes a means for allowing passage of air from said second container.

* * * * *